US006805453B2

United States Patent
Spetzler et al.

(10) Patent No.: US 6,805,453 B2
(45) Date of Patent: Oct. 19, 2004

(54) MEDICAL INSTRUMENT ARRANGEMENT WITH DRAPE

(75) Inventors: Robert F. Spetzler, Paradise Valley, AZ (US); Jeremy Diringer, Ithaca, NY (US); Günther Grubauer, Neresheim (DE); Klaus Gottwaldt, Oberkochen (DE); Kirsten Stäbler, Aalen (DE)

(73) Assignee: Carl-Zeiss-Stiftung, Heidenheim (DE)

( * ) Notice: Subject to any disclaimer, the term of this patent is extended or adjusted under 35 U.S.C. 154(b) by 131 days.

(21) Appl. No.: 10/246,477

(22) Filed: Sep. 19, 2002

(65) Prior Publication Data

US 2003/0066534 A1 Apr. 10, 2003

Related U.S. Application Data

(60) Provisional application No. 60/323,308, filed on Sep. 20, 2001.

(51) Int. Cl.$^7$ ................................................ G03B 11/04
(52) U.S. Cl. ........................ 359/510; 359/511; 359/512; 359/513
(58) Field of Search .................................. 359/510–513, 359/368, 373; 128/849, 856, 883; 348/65, 77, 373; 601/109, 112–113, 131

(56) References Cited

U.S. PATENT DOCUMENTS

| | | | |
|---|---|---|---|
| 5,122,904 A | 6/1992 | Fujiwara et al. | |
| 5,239,981 A | 8/1993 | Anapliotis | |
| 5,458,132 A | 10/1995 | Yabe et al. | |
| 5,873,814 A | 2/1999 | Adair | |
| 5,970,980 A | 10/1999 | Adair | |
| 6,129,319 A | 10/2000 | Metelski | |

OTHER PUBLICATIONS

"Two Technical Notes for Microsurgery" by R. F. Spetzler, BNI Quarterly, vol. 4, No. 2, Spring 1988, pp. 38 and 39.

Primary Examiner—Mohammad Sikder
(74) Attorney, Agent, or Firm—Walter Ottesen

(57) ABSTRACT

A medical instrument arrangement includes an operation microscope system (100) and a carrier unit (101) carrying the operation microscope (102). The medical instrument arrangement is at least partially covered by a drape (110). The air inside the drape (110) is removed by a suction unit. The drape (110) is fixed to a portion of the carrier unit (101) at a collar (115). By operating the suction unit at different suction rates, disturbing vibrations of the system during a surgical procedure can be minimized.

16 Claims, 3 Drawing Sheets

MEDICAL INSTRUMENT ARRANGEMENT WITH DRAPE

RELATED APPLICATION

This application claims the benefit of U.S. Provisional Application No. 60/323,308, filed Sep. 20, 2001.

FIELD OF THE INVENTION

This invention relates to a medical instrument arrangement, for example, a medical instrument for use in surgical operations carried out under sterile conditions. This instrument arrangement includes a carrier unit carrying an instrument unit, a drape covering the instrument unit at least partially and a suction unit for removing medium from the drape. This invention further relates to a method for operating such instrument arrangement.

BACKGROUND OF THE INVENTION

In surgical operations various medical instruments are used. The parts of such instruments which are exposed to a field of operation have to be sterile. Generally, on an optical microscope this is achieved by a transparent, sterile drape placed around the optical setup of the instrument. In the region of the objective lens system of microscope, such drape has a window opening for allowing a good and clear view of the field of operation. However, due to its bulkiness, such drape may restrict the view on the field of operation both for the surgeon and the assistants. A bulky drape reduces the space between the field of operation and the medical instrument where various operating tools are manipulated and passed. Furthermore, a bulky drape may be a handicap for a surgeon or an assistant to work or pass below a carrier arm of the instrument which is protected by the drape. In addition, the handling and actuation of control buttons of the medical instrument which lie under the drape is uncomfortable and may lead to errors in manipulation if there is a bulky drape around the medical instrument.

In "BNI QUARTERLY" vol. 4 (2), 1988, it has been suggested to use suction for eliminating the disturbing bulkiness of such a drape placed around an operation microscope used in surgical operations. It is reported that such suction can be carried out by attaching a suction tube to the frame of the microscope-head while snugly closing the end of the drape at the horizontal arm of the microscope stand with a Penrose drain. With the drape deflated, it assumes the outline of the original microscope and stand. The deflated microscope drape increases the visual field of the operating nurse and assistant and allows them greater access to pass instruments underneath or around the microscope.

SUMMARY OF THE INVENTION

The object of the invention is to provide an instrument arrangement which can be equipped with a sterile drape while allowing for easy handling and to provide a method for operating such instrument in a way that negative effects of the drape on a surgical operation or procedure are minimized.

This object is achieved by an instrument arrangement having a carrier unit carrying an instrument unit and packing means provided on a portion of the carrier unit to which a drape can be fixed, while there is a suction unit for removing medium from the drape. Such packing can have the form of a collar, of a sleeve or the like. The packing can be provided with pass-throughs for suction tubes and allows for a more or less gastight closure of the drape to the microscope stand. If the drape is fixed to the collar by means of a VELCRO fastening, a tape or the like, such drape can be changed easily and rapidly for sterilization. The suction unit of the instrument may include a pump which is arranged in a stand or ceiling mount of the instrument in a way that pumping vibrations are not transmitted to the instrument unit. Alternatively, the suction unit may be designed to be connected to some external stationary pumping unit as in a standard operating room in general.

In a preferred embodiment there is a suction unit with an exit for medium removed from the drape, which is arranged at a clear and safe distance from the instrument unit. In this way, the air drawn out of the drape is guided and discharged far away from the field of operation and infections of a surgical wound can be avoided.

If the suction unit includes a pump with a turbine, vibrations related to suction which disturb the view of the surgeon through an operation microscope can be minimized.

Preferably the suction unit is at least partially integrated into the carrier unit and into the instrument unit. Such suction unit allows for a compact design of a medical instrument and for a medical instrument which can be transported easily.

In a preferred embodiment of the instrument arrangement, means to control a suction rate are provided. Such instrument allows for adapting a suction rate to an instantaneous leak rate.

Very effective suction of air from the drape can be achieved in that one or more openings for removing medium from the drape are provided in the suction unit.

In another preferred embodiment of the instrument arrangement, means are provided for preventing obstruction of the one or more openings of the suction unit by the drape. In this way, a very reliable medical instrument is provided.

Preferably, there are means for ventilating the drape. These means for ventilating the drape may include a valve or a pump, for example, a turbo engine or the like which not only removes fluid but can be reversed as well. Such instrument allows for easy and fast change of the drape between two surgical operations.

If there is a suction unit with a tube in the instrument arrangement which is at least partially bendable, the tube system has no negative impact on the maneuverability of a microscope stand. It is also possible to provide a pipe system having link joints for the suction unit. Such instrument arrangement has a very solid system for removing air from the drape.

A method for operating a corresponding instrument arrangement includes the steps of removing medium from a drape at least partially covering an instrument unit of the instrument by means of a suction unit at a first suction rate in a first operating state of the instrument and removing medium from a drape at least partially covering an instrument unit of the instrument by means of a suction unit at a second suction rate in a second operating state of the instrument, the first suction rate being greater than the second suction rate. Such method allows for a rapid preparation of the instrument for a surgical operation.

By ventilation, the drape around the instrument can be removed easily in order to replace it by a new, sterile one.

BRIEF DESCRIPTION OF THE DRAWINGS

The invention will be described in detail for several embodiments, all in conjunction with the accompanying drawings, in which.

DESCRIPTION OF THE PREFERRED EMBODIMENTS OF THE INVENTION

Figure 1:
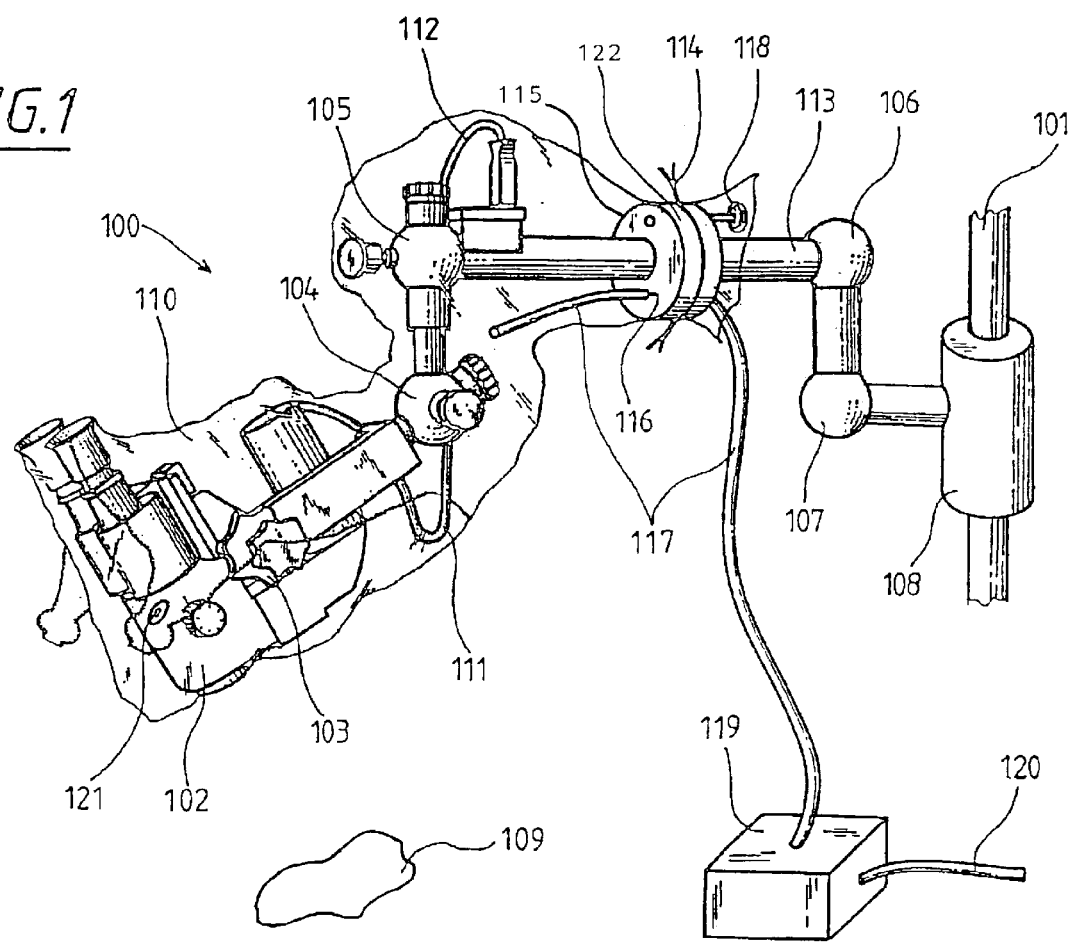
FIG. 1 is a perspective view of an operation microscope system with a drape and an external suction unit.

FIG. 1 shows, as a medical instrument arrangement, an operation microscope system 100. This operation microscope system 100 includes a microscope stand 101 as a carrier unit for an instrument unit in the form of the operation microscope 102. The microscope stand 101 may be a floor stand or a ceiling mount. The operation microscope 102 has several link joints 103, 104, 105, 106, 107 and 108 allowing for deliberate positioning of the operation microscope 102 with respect to some field of operation 109.

For use in a sterile working atmosphere, the operation microscope system 100 is partially covered with a sterile drape 110. Such sterile drape 110 allows that the portion of the microscope system 100, which is covered by the drape 110, does not have to be sterile. This portion of the microscope system 100 includes the link joints 103, 104, 105 and the cable connections 111 and 112, which are difficult to sterilize or even cannot be sterilized at all.

At a distance from the field of operation 109, the sterile drape 110 is fixed to an arm 113 of the microscope stand 101 as a portion of the carrier unit by a VELCRO fastening 114 attached to a collar 115. The space enclosed by the drape 110 is sealed by means of the collar 115. This collar forms a gastight connection to the arm 113 of the microscope stand. At the collar 115 a valve 118 is provided which, when actuated, allows for venting the region enclosed by the drape 110.

The collar 115 defines a barrier to the unsterilized portion of the instrument enclosed by the drape 110. The collar defines a smooth peripheral cylindrical surface 122 against which the drape is pressed with the VELCRO fastening 114 thereby forming a gastight connection. Thus, the collar 115 performs the dual function of providing a barrier to the unsterilized portion of the instrument and defining a smooth attachment surface 122 for the drape.

The operation microscope system 100 comprises a suction unit having a suction tube 117 and a pump 119 for a fluid medium. The suction tube 117 is passed through an opening 116 of the collar 115. The pump 119 is designed as a turbo engine in order to minimize the transfer of pumping vibrations to the microscope stand 101. A pump suitable for this purpose is available from Werner Rietschle GmbH & Co. KG of Schopfheim, Germany, under product number 102631-0111 (CHILISGP 16(01)).

As an alternative, any system for pumping fluid medium may be used. To avoid that the maneuverability of the microscope stand 101 is hindered by the suction tube, the suction tube 117 is made of a flexible material, for example, rubber or soft plastic. There is an exhaust tube 120 having an opening arranged at a clear and safe distance from the field of operation 109. In this way, air pumped out of the drape 110 covering the operation microscope 102 is guided far away from the field of operation 109 thereby lowering the risk of infection. The portion of the system covered by the drape will, in general, not be sterile.

The operation microscope 102 has a control button 121 for controlling the pump and setting a suitable pump rate. This control button 121 is connected to the pump 119. There is a pressure sensor not shown in FIG. 1, which senses the pressure under the drape as soon as the pump 119 is activated by the control button. This pressure sensor provides a control signal for adapting the pump rate to the present pressure. If, for example, the pressure sensor determines that the pressure drops during a surgical operation in a low-load state of the pump 119, then the pump 119 is switched to high-load for again reaching the ideal state. The pump switches to a low-load state automatically when the pressure sensor again detects the ideal state. As an alternative or in addition, a touch screen or speech control may be provided for controlling suction at the instrument.

For making the operation microscope system ready for a surgical operation, a sterile collar 115 is placed around the arm 113 of the microscope stand 101. A tube 117 connected to the pump 119 is inserted through the opening 116 of the collar 115. Then a sterile drape 110 is placed around the operation microscope 102 and portions of the stand 101. An end portion of this drape is fixed to the arm 113 of the stand by means of the collar 115 making use of a VELCRO fastening 114 or the like. With the valve 118 at the collar 115 closed, the spatial region enclosed by the drape 110 is evacuated at a first high-load rate by the pump 119.

Figure 2:
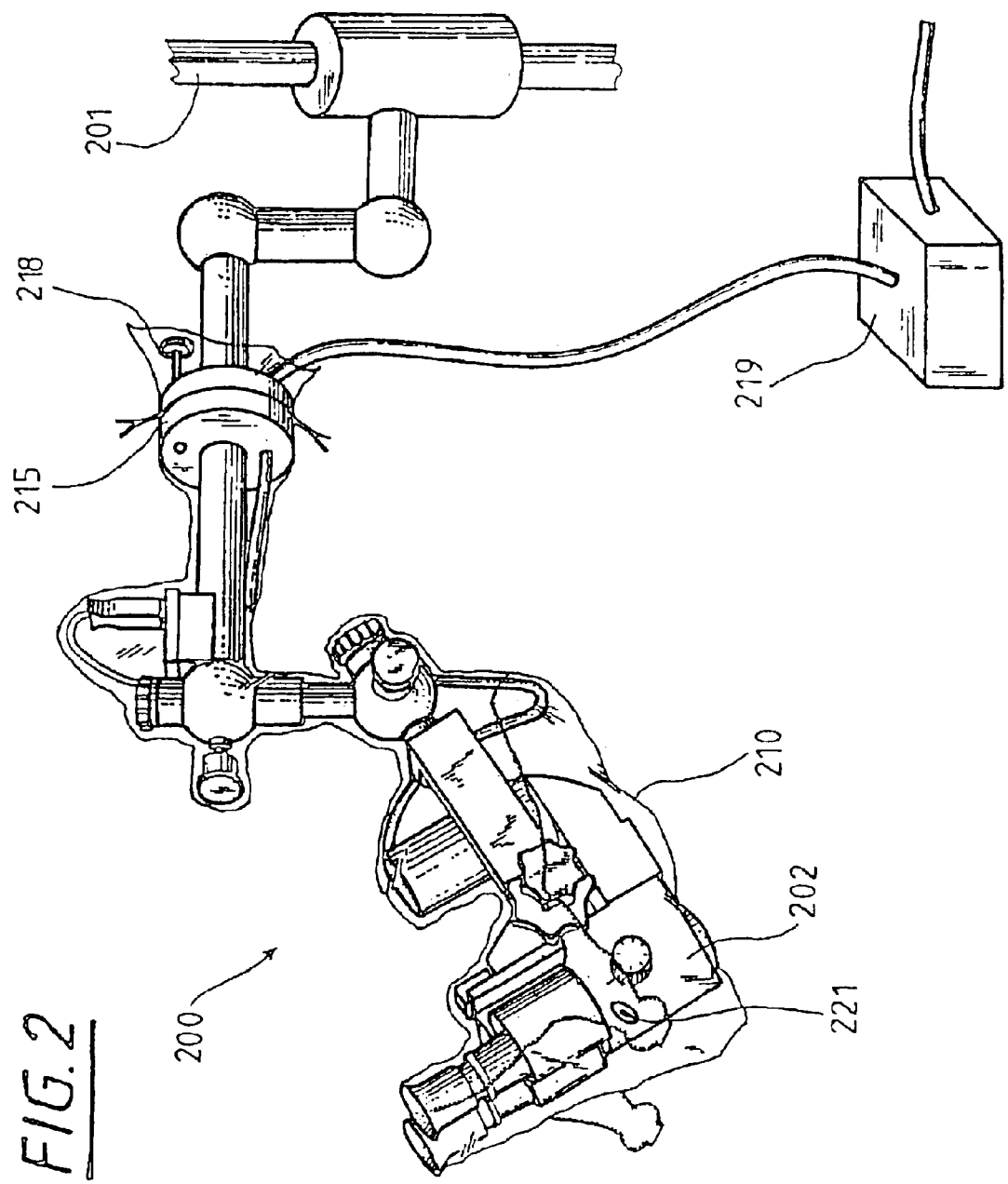
FIG. 2 is a view of the operation microscope system shown in FIG. 1 with air removed from the drape.

FIG. 2 shows the drape of the operating microscope system of FIG. 1 in a deflated or evacuated condition. The drape 210 around the operating microscope system 200 is evacuated and assumes the outline of the operation microscope 202 and the portions of the stand 201 covered by the drape 210. In response to a signal of the pressure sensor, as soon as the drape 210 assumes the outline of the operation microscope and the corresponding stand, the pump is switched to a low-load state of operation. In this low-load state of operation, air is removed from the drape 210 at a reduced rate, which is less than the high-load rate because, when the drape 210 assumes the outline of the operation microscope 202 and the portions of the stand 201, it is sufficient to remove the gas entering by leak openings. As an alternative to switching the pump to the low-load state automatically in response to a suitable pressure value sensed by a pressure sensor, the corresponding pumping rate may be set by actuating a control button.

In this way, disturbing vibrations due to the pumping process are minimized and do not affect the optical view of a surgeon through the microscope.

For allowing easy removal of the drape 210 after a surgical procedure, the valve 218 at the collar 215 is in an open condition venting the drape 210.

Figure 3:
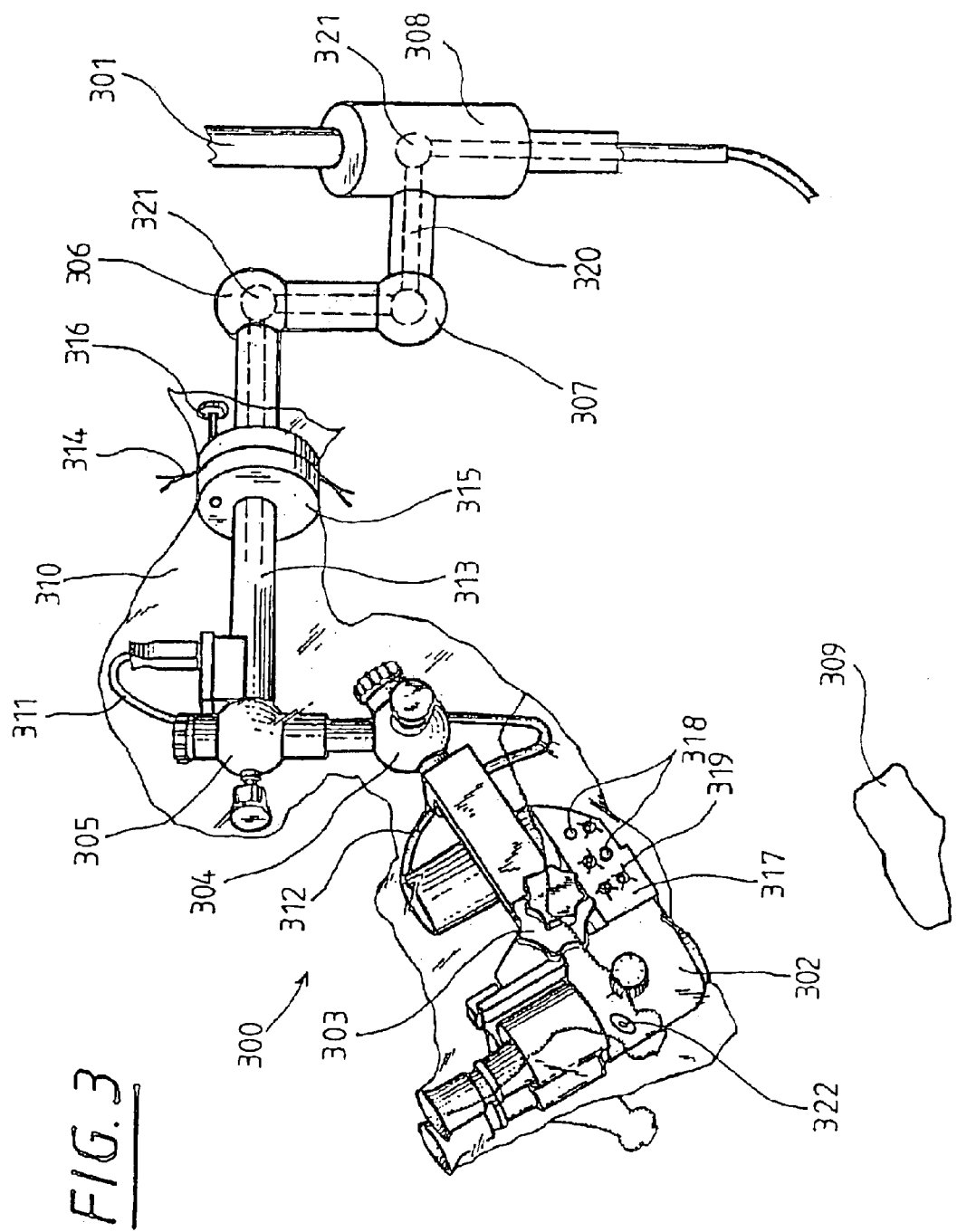
FIG. 3 is a view of an operation microscope system with a drape and a suction unit integrated into the microscope stand.

FIG. 3 shows another medical instrument arrangement formed by an operation microscope system 300 having a basic setup which is similar to the operation microscope system of FIG. 1.

The operation microscope system 300 has a microscope stand 301. This microscope stand 301 can be a floor stand or a ceiling stand. It comprises link joints 303, 304, 305, 306, 307 and 308 which permit the operation microscope 302 to be deliberately positioned in any direction with respect to a field of operation 309.

As for the operation microscope system described with respect to FIGS. 1 and 2, a sterile drape 310 is provided for covering portions of the system, which are difficult to sterilize, such as cable connections 311 and 312.

The drape 310 is tightly fixed to the arm 313 of the operation microscope 302 by a VELCRO fastening 314 or the like and attached to a collar 315 provided on the arm 313 of the instrument. The collar 315 includes a valve 316 which can be actuated to open and close a passage through that collar 315. The spatial region enclosed by the drape 310 is separated from the outer atmosphere in a more or less gastight way.

The operation microscope system 300 comprises a suction unit, which, different from the microscope system described with respect to FIGS. 1 and 2, is partly integrated into the microscope stand 301 and into the operation microscope 302.

This suction unit has a pump which is arranged in a part 317 of the microscope. At this part 317, suction openings 318 are provided for removing air from the interior of the drape 310. Around these suction openings 318, means 319 are arranged which prevent the suction openings 318 from being blocked by the drape 310 while air is pumped out. As an alternative, the pump may be arranged inside an arm of the operation microscope system next to the microscope stand 301.

For allowing compact dimensions of the microscope system, the pump is designed as a turbo engine. Apart from good load performance, such a pump causes only little vibration with a frequency spectrum having no negative effect on the optical view of an observer through the operation microscope. The pump is designed to be operated at different suction rates, which, for example, can be set by an operating button 322 as explained on the operation microscope system shown in FIG. 1.

The air pumped from the region enclosed by the drape 310 is guided in a pipe system 320 arranged in the interior of the microscope stand 301 and routed away from the field of operation. The pipe system 320 comprises ball joints 321 at the corresponding link joints of the microscope stand 301. These ball joints allow for an easy maneuverability of the microscope stand with the tube system inside and provide a long lasting system to remove air from the drape 310.

As an alternative to venting the drape 310 by actuating a valve 316, the drape 310 may be vented by running the pump in a reverse state where air from outside is pumped into the region enclosed by the drape 310.

It is understood that the foregoing description is that of the preferred embodiments of the invention and that various changes and modifications may be made thereto without departing from the spirit and scope of the invention as defined in the appended claims.

What is claimed is:

1. A medical instrument arrangement for use in a surgical procedure carried out on a patient under sterile conditions, the medical instrument arrangement comprising:

a surgical instrument for use by a surgeon during the surgical procedure;

a carrier unit for supporting said surgical instrument;

said surgical instrument having surfaces which are unsterilized;

said carrier having a mounting structure thereon defining a barrier disposed between the unsterilized surgical instrument and the ambient;

said mounting structure defining a smooth surface extending over the periphery thereof;

a gastight sterile drape completely enclosing the unsterilized surfaces of said surgical instrument; and, an attachment device for attaching said drape to said mounting structure at said smooth surface thereof so as to provide a gastight interface between said drape and said smooth surface thereby preventing an infection of the patient from said unsterilized surfaces during the surgical procedure.

2. The medical instrument arrangement of claim 1, wherein said attachment device is a VELCRO fastener.

3. The medical instrument arrangement of claim 1, further comprising a suction unit for at least partially removing a medium from the spatial region enclosed by said drape.

4. The medical instrument arrangement of claim 3, wherein said suction unit is provided with an outlet for medium removed from said drape, which is arranged at a distance from said surgical instrument.

5. The medical instrument arrangement of claim 3, wherein said suction unit comprises a suction pump having a turbine.

6. The medical instrument arrangement of claim 3, wherein said suction unit is at least partially integrated in said carrier unit.

7. The medical instrument arrangement of claim 3, wherein said suction unit is at least partially integrated into said medical instrument.

8. The medical instrument arrangement of claim 3, further comprising means for controlling a suction rate of said suction unit.

9. The medical instrument arrangement of claim 3, wherein said suction unit comprises at least one opening for removing medium from said spatial region.

10. The medical instrument arrangement of claim 9, wherein means are provided for avoiding obstruction of said at least one opening of the suction unit by said drape.

11. The medical instrument arrangement of claim 3, wherein means for venting said drape are provided.

12. The medical instrument arrangement of claim 3, wherein the said suction unit comprises a tube communicating with said spatial region for conducting away said medium therefrom; and, said tube being mounted on said carrier unit is at least partially bendable so as to follow movements of said carrier unit.

13. The medical instrument arrangement of claim 3, wherein said suction unit comprises a pipe system communicating with said spatial region for conducting away said medium therefrom; and, said pipe system is mounted on said carrier unit and includes a plurality of segments interconnected by joints to permit said pipe system to follow movements of said carrier unit.

14. The medical instrument arrangement of claim 3, wherein said carrier unit includes an arm assembly on which said surgical instrument is mounted; said mounting structure is a collar mounted on one of the arms of said arm assembly; and, said collar has an annular periphery defining said smooth surface.

15. The medical instrument arrangement of claim 14, wherein said suction unit includes a suction line mounted in said collar and communicating with said spatial region.

16. The medical instrument arrangement of claim 15, further comprising a venting valve mounted in said collar for venting said spatial region enclosed by said drape.

\* \* \* \* \*